Aug. 6, 1957 C. F. PENNOCK Plant Pat. 1,627
DRACAENA PLANT
Filed Aug. 28, 1956
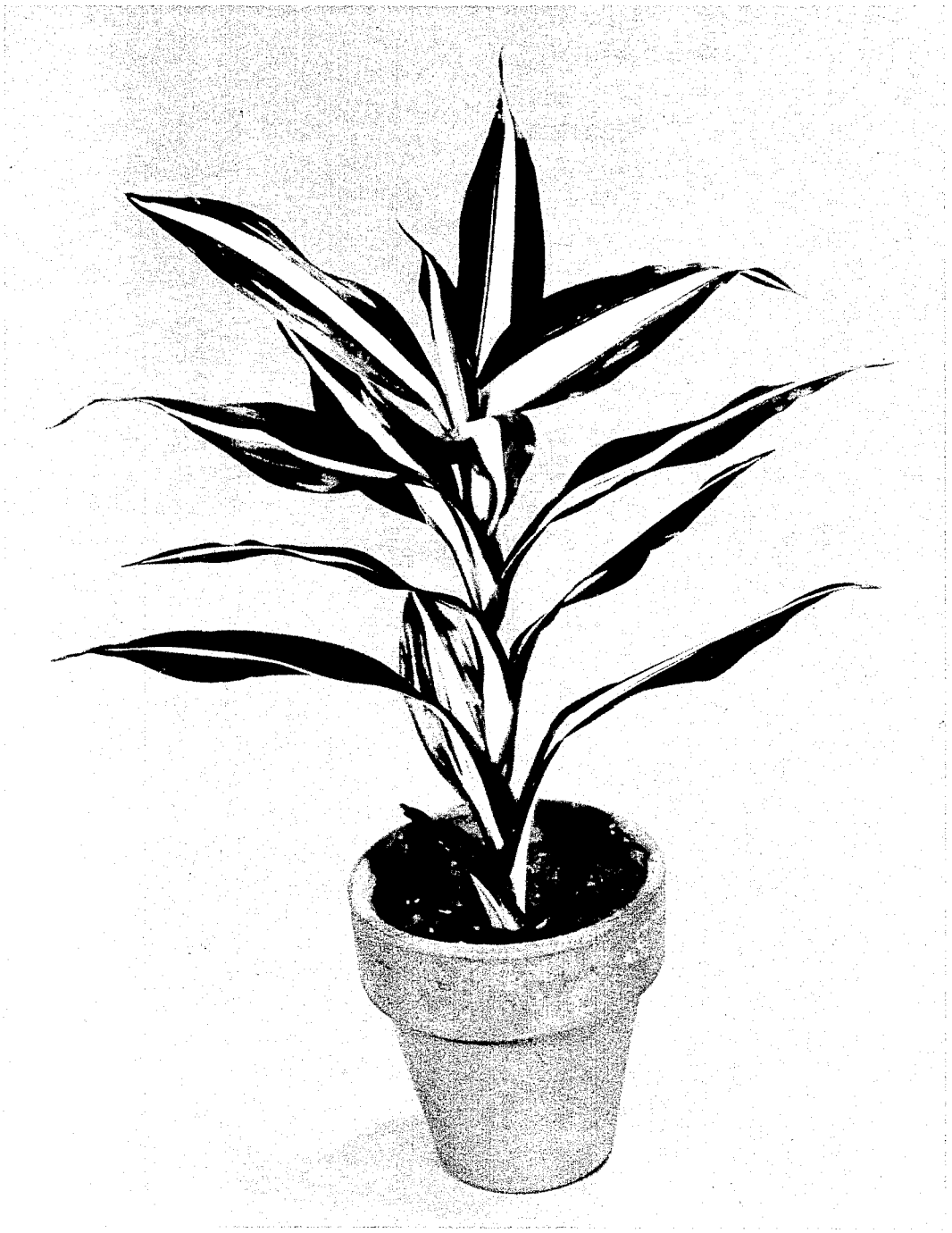
INVENTOR
Charles F. Pennock
By Orville M. Kile
Plant Pat. Agt.

United States Patent Office

Plant Pat. 1,627
Patented Aug. 6, 1957

1,627

DRACAENA PLANT

Charles F. Pennock, Rio Piedras, San Juan, Puerto Rico

Application August 28, 1956, Serial No. 606,789

1 Claim. (Cl. 47—59)

My discovery relates to a new and distinct variety of ornamental plant known as Dracaena, and originated as a sport of the variety *Dracaena sanderiana* (unpatented). The sport was discovered by me in San Juan. It has been asexually reproduced by me at the same location, by means of cuttings, and its distinguishing features appear to be permanent.

The accompanying illustration shows a color photograph of a potted plant of this new variety in approximately its true colors, the plant shown being about seven weeks old at the time of photographing. The specimen was at that time approximately 8½ inches tall from the ground to the tip of the central leaf.

In the following detailed description of my new variety, color plate numbers refer to Ridgway's Color Standards and Nomenclature, whereas other reference to color indicates the usual dictionary meaning.

My new variety is an herbaceous plant and has small narrow lanceolate leaves of from 7 to 10 inches in length and ½ to 1½ inches in width. The leaves are rather compactly grouped, but if the plant is allowed to grow without being cut back, the internodes elongate slightly as the plant grows, although this is not a readily noticeable trait. The plant grows very straight and erect, with its leaves very regularly spaced. If allowed to grow without cutting back, it will grow about 12 inches the first year.

Because of its dwarf size and pleasing color pattern, my new variety makes an excellent house plant. It propagates true from cuttings, rooting readily at each node which is below the earth's surface.

The outstanding features of my new variety are the deep green coloring and novel striping of the leaves, together with the straight, erect growth. The green of my new variety is much darker than that of the parent variety, being approximately Dark Dull Yellow Green (Plate XXXII). There is a band of white or yellowish-white extending lengthwise through the center of each leaf, edged on both sides by a generous stripe of dark green usually of width similar to the white stripe.

The leaves are ridged parallel with the midrib and are heavier in texture than those of the parent variety.

The newest leaf stands perpendicular at the top of the plant, and the next two leaves, or perhaps three, stand almost perpendicular. But the rest of the leaves are approximately horizontal, or even recurved in some instances.

*Comparisons*

The variety most like my new variety is the *Dr. borinquensis* (not patented), also developed by me and recently placed on the market. This variety is likewise a sport of *D. sanderiana*. The principal differences between the two varieties lie in the color patterns of their leaves, as follows:

1. The color pattern of the leaves of my new variety consists of a broad white or yellowish-white band through the center of the entire length of the leaf, which is broadly margined with very dark green, whereas the *Dr. borenquensis* variety has a light silvery-green band lengthwise of the center of the leaf between the two dark green stripes which form the margins.

2. On most of the leaves of the *Dr. borenquensis*, at the precise demarkation line between the silvery-green and the dark-green, there is a very fine white or yellowish-white stripe, whereas my new variety does not have this fine stripe separating the two bands of color.

3. *Dr borinquensis* is a slightly stronger grower, probably due to the greater amount of chlorophyll in its make-up.

Another variety similar to my new variety is its parent, *D. sanderiana*, the two differing principally as follows:

1. The color patterns of the two varieties differ in that my new variety has a white or yellowish-white band down the center of the entire length of the leaf, broadly margined with very dark green stripes, whereas the parent variety has the pattern reversed.

2. The green of the leaves of my new variety is much darker than that of the parent variety.

3. The leaves of the parent variety frequently have an additional fine line of white between the broad bands, whereas this is not a characteristic feature of my new variety.

4. The leaves of my new variety are heavier in texture than those of the parent variety.

5. The leaves of my variety are not so smooth, due to the lengthwise ridges.

Having thus disclosed my discovery, I claim:

The new and distinct variety of Dracaena plant, substantially as herein shown and described, characterized particularly by its upright, erect growth; its dwarf, compact form; its heavy-textured leaves ridged lengthwise; and the distinctive color pattern of its leaves with a broad, essentially-white stripe lengthwise through the center, and broadly margined with very dark green.

No references cited.